(12) United States Patent
Higashi (10) Patent No.: US 8,802,627 B2
(45) Date of Patent: Aug. 12, 2014

(54) FUSION PROTEIN COMPOSED OF MATRIX METALLOPROTEINASE-2 INHIBITOR PEPTIDE DERIVED FROM AMYLOID-B PRECURSOR PROTEIN AND TISSUE INHIBITOR OF METALLOPROTEINASE-2

(75) Inventor: Shouichi Higashi, Yokohama (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 13/123,210

(22) PCT Filed: Oct. 5, 2009

(86) PCT No.: PCT/JP2009/067320
§ 371 (c)(1),
(2), (4) Date: Apr. 7, 2011

(87) PCT Pub. No.: WO2010/041617
PCT Pub. Date: Apr. 15, 2010

(65) Prior Publication Data
US 2011/0195902 A1  Aug. 11, 2011

(30) Foreign Application Priority Data
Oct. 9, 2008 (JP) .................................. 2008-262415

(51) Int. Cl.
| *A61K 38/00* | (2006.01) |
| *C12P 21/04* | (2006.01) |
| *C07K 14/81* | (2006.01) |
| *C07K 14/47* | (2006.01) |

(52) U.S. Cl.
CPC ......... *C07K 14/4711* (2013.01); *C07K 14/8146* (2013.01); *A61K 38/00* (2013.01); *C07K 2319/70* (2013.01)
USPC ....... 514/13.3; 514/16.4; 514/19.8; 435/69.7; 530/350

(58) Field of Classification Search
CPC . A61K 38/00; C07K 14/8146; C07K 2319/70
See application file for complete search history.

(56) References Cited

U.S. PATENT DOCUMENTS

| 5,595,885 A | 1/1997 | Stetler-Stevenson et al. ............................ 435/69.2 |
| 2003/0073217 A1 | 4/2003 | Barr et al. ..................... 435/184 |
| 2008/0181892 A1 | 7/2008 | Ledbetter et al. .......... 424/134.1 |

FOREIGN PATENT DOCUMENTS

| WO | WO 90/11287 | 10/1990 |
| WO | WO 02/50287 A2 | 6/2002 |
| WO | WO 2007/011363 A2 | 1/2007 |

OTHER PUBLICATIONS

Higashi et al., Identification of a Region of β-Amyloid Precursor Protein Essential for Its Gelatinase A Inhibitory Activity, The Journal of Biological Chemistry, vol. 278, No. 16 (Apr. 18, 2003).*

(Continued)

*Primary Examiner* — Christina Bradley
*Assistant Examiner* — Randall L Beane
(74) *Attorney, Agent, or Firm* — Bingham McCutchen LLP (57) ABSTRACT

The present invention provides an agent capable of inhibiting MMP-2 specifically. Disclosed is a fusion molecule composed of a β-amyloid precursor protein molecule-derived domain having an activity of selectively inhibiting matrix metalloproteinase-2 and a tissue inhibitor of metalloproteinase capable of binding to latent matrix metalloproteinase. Also disclosed are a pharmaceutical composition, a cancer metastasis and/or angiogenesis inhibitor, a therapeutic and/or prophylactic for cardiovascular diseases, and a matrix metalloproteinase-2 inhibitor, each of which comprises the fusion molecule.

2 Claims, 2 Drawing Sheets

Enzyme specificity in inhibitory activity of APP-IP-TIMP-2

(56) References Cited

OTHER PUBLICATIONS www.ncbi.nlm.nih.gov/, attached as pdf, also available at http://www.ncbi.nlm.nih.gov/protein (search term "TIMP2")(last visited Dec. 7, 2012).*

Shouichi Higashi et al., "Identification of a Region of β-Amyloid Precursor Protein Essential for Its Gelatinase A Inhibitory Activity", The Journal of Biological Chemistry, vol. 278, No. 16, Apr. 18, pp. 14020-14028, 2003.

Translation of International Preliminary Report on Patentability and Written Opinion of the International Searching Authority.

Hideaki Nagase et al., "Structure and fusion of matrix metalloproteinases and TIMPs" Cardiovascular Research, vol. 69, No. 3, pp. 562-573, Feb. 15, 2006.

Shouichi Higashi et al., "Identification of Amino Acid Residues of the Matrix Metalloproteinase-2 Essential for Its Selective Inhibition by Beta-Amyloid Precursor Protein-derived Inhibitor" Journal of Biological Chemistry, vol. 238, No. 15, pp. 10068-10078, Apr. 2008.

Woo Kyu Kang et al., "A biologically active angiogenesis inhibitor, human serum albumin-TIMP-2 fusion protein, secreted from *Saccharomyces cerevisiae*" Protein Expression and Purification, vol. 53, No. 2, pp. 331-338, Mar. 2007.

N. Zouti et al., "Selective inhibition of matrix metalloproteinase 2 (gelatinase A) by barium chloride" Analytical Biochemistry, vol. 350, No. 1, pp. 159-161, Mar. 2006.

Gautier Moroy et al., "Simultaneious presence of unsaturation and long alkyl chain at P1<'> of Ilomastat confers selectivity for gelatinase A (MMP-2) over gelatinase B (MMP-9) inhibition as shown by molecular modelling studies" Bioorganic & Medicinal Chemistry, vol. 15, No. 14, pp. 4753-4766, Jul. 15, 2007.

Ivan Sandowski, "Protein Domain Fusion" Encyclopedia of Life Sciences, pp. 1-7, Apr. 1, 2001.

Vaskar Saha et al., "Fusion Proteins and Diseases" Encyclopedia of Life Sciences, pp. 1-8, 2005.

Hiroshi Hashimoto et al., "Structural Basis for Matrix Metalloproteinase-2 (MMP-2)-selective Inhibitory Action of beta-amyloid Precursor Protein-derived Inhibitor" Journal of Biological Chemistry, vol. 286, No. 38, pp. 33236-33243, Sep. 2011.

Extended European search report dated Aug. 22, 2012 issued in corresponding European application 09819151.3 cites the non-patent literature above.

* cited by examiner

Fig. 1

FUSION PROTEIN COMPOSED OF MATRIX METALLOPROTEINASE-2 INHIBITOR PEPTIDE DERIVED FROM AMYLOID-Β PRECURSOR PROTEIN AND TISSUE INHIBITOR OF METALLOPROTEINASE-2

TECHNICAL FIELD

The present invention relates to a fusion protein composed of a matrix metalloproteinase-2 inhibitor peptide derived from β-amyloid precursor protein and a tissue inhibitor of metalloproteinase, as well as use of the fusion protein. More specifically, the present invention relates to a fusion molecule comprising a β-amyloid precursor protein molecule-derived domain having an activity of selectively inhibiting matrix metalloproteinase-2 and a tissue inhibitor of metalloproteinase capable of binding to latent matrix metalloproteinase-2, as well as use of the fusion molecule.

BACKGROUND ART

Matrix metalloproteinases (MMPs) are proteolytic enzymes having high degradation activity against extracellular matrix proteins and are considered to support cell migration during cancer invasion and metastasis (Non-Patent Document No. 1). On the other hand, the results of analyses using knockout mice have suggested that MMP-2 enhances angiogenesis in tumor tissue (Non-Patent Document No. 2). Therefore, MMPs are good target molecules for developing cancer metastasis inhibitors and cancer growth inhibitors. To date, a large number of MMP inhibitors based on hydroxamic acid derivatives have been developed by pharmaceutical companies, etc.

It has been found that because of their low specificity, these conventionally developed MMP inhibitors inhibit not only their target MMP but also other MMPs in the body, thus producing unexpected side effect. For this reason, most of pharmaceutical companies have retreated from the development of MMP inhibitors. Besides, some of MMPs inhibit cancer invasion and metastasis. Therefore, if inhibitors with low specificity inhibit all MMPs, the effect of inhibition of their target MMP will be offset and, even worse, there is a possibility that cancer metastasis might be enhanced.

[Non-Patent Document No. 1]
Werb, Z. (1997) Cell 91, 439-442
[Non-Patent Document No. 2]
Ito, T. et al. (1998) Cancer Res. 58, 1048-1051

DISCLOSURE OF THE INVENTION

Problem for Solution by the Invention

It is an object of the present invention to provide an agent capable of specifically inhibiting MMP-2.

Means to Solve the Problem

Figure 2:
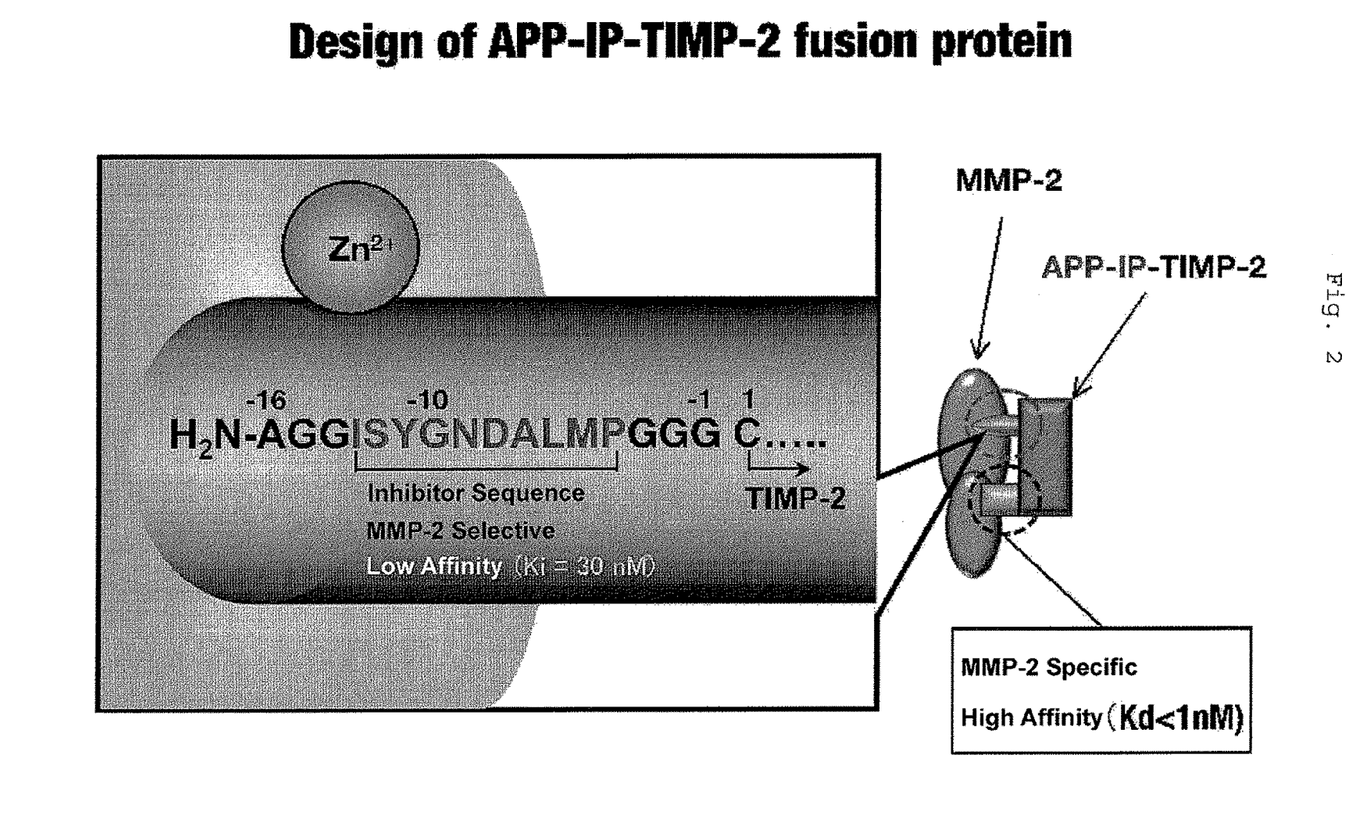
FIG. 2 is a schematic view showing the design of APP-IP-TIMP-2 fusion protein.

The present inventor has found that a partial amino acid sequence ISYGNDALMP in β-amyloid precursor protein (APP) molecule (APP-derived inhibitory peptide: APP-IP) has MMP-2 selective inhibitory activity (THE JOURNAL OF BIOLOGICAL CHEMISTRY, Vol. 278, No. 16, April 18, pp. 14020-14028, 2003). This APP-IP inhibits MMP-2 activity in a different inhibition mode than conventional hidroxamic acid-based MMP inhibitors or natural inhibitor proteins TIMPs. It has become clear that a fusion protein composed of APP-IP and a tissue inhibitor of metalloproteinase capable of binding to latent MMP-2 (e.g., TIMP-2) (FIG. 2) works as an MMP-2 inhibitor of high affinity and high specificity because the MMP-2 binding site of the tissue inhibitor of metalloproteinase capable of binding to latent MMP-2 and the MMP-2 selective inhibition site of APP-IP are utilized in a complementary manner. The present invention has been achieved based on these findings.

The present invention may be summarized as follows.

(1) A fusion molecule comprising a β-amyloid precursor protein molecule-derived domain having an activity of selectively inhibiting matrix metalloproteinase-2 and a tissue inhibitor of metalloproteinase capable of binding to latent matrix metalloproteinase-2.

(2) The fusion molecule of (1) above, wherein 1 to 10 amino acids are added to the N-terminus and/or C-terminus of the β-amyloid precursor protein molecule-derived domain having an activity of selectively inhibiting matrix metalloproteinase-2.

(3) The fusion molecule of (1) or (2) above, wherein the tissue inhibitor of metalloproteinase capable of binding to latent matrix metalloproteinase-2 is selected from the group consisting of tissue inhibitors of metalloproteinase-2, -3 and -4.

(4) A DNA encoding the fusion molecule of (1) above.

(5) A vector comprising the DNA of (4) above.

(6) A transformant comprising the vector of (5) above.

(7) A method of preparing a fusion molecule, comprising culturing the transformant of (6) above.

(8) A pharmaceutical composition comprising the fusion molecule of (1) above.

(9) A cancer metastasis and/or angiogenesis inhibitor comprising the fusion molecule of (1) above.

(10) A therapeutic and/or prophylactic for cardiovascular diseases, comprising the fusion molecule of (1) above.

(11) The therapeutic and/or prophylactic of (10) above, wherein the cardiovascular disease is selected from the group consisting of myocardial infarction, arteriosclerosis and hypertrophic cardiomyopathy.

(12) A matrix metalloproteinase-2 inhibitor comprising the fusion molecule of (1) above.

(13) A method of inhibiting cancer metastasis and/or angiogenesis, comprising administering the fusion molecule of (1) above.

(14) A method of treating and/or preventing cardiovascular diseases, comprising administering the fusion molecule of (1) above.

(15) A method of inhibiting matrix metalloproteinase-2, comprising using the fusion molecule of (1) above.

(16) The fusion molecule of (1) above for use as a medicine.

(17) The fusion molecule of (1) above for use in inhibiting cancer metastasis and/or angiogenesis.

(18) Use of the fusion molecule of (1) above for manufacturing a cancer metastasis and/or angiogenesis inhibitor.

(19) The fusion molecule of (1) above for use in treating and/or preventing cardiovascular diseases.

(20) Use of the fusion molecule of (1) above for manufacturing a therapeutic and/or prophylactic for cardiovascular diseases.

(21) The fusion molecule of (1) above for use as a matrix metalloproteinase-2 inhibitor.

(22) Use of the fusion molecule of (1) above for manufacturing a matrix metalloproteinase-2 inhibitor.

Unlike conventional MMP inhibitors with low specificity, the fusion protein of the present invention is an MMP-2 inhibitor with extremely high specificity, so there is high likelihood that this inhibitor can be used as an effective cancer metastasis and angiogenesis inhibitor with an extremely small adverse effect.

Effect of the Invention

The fusion protein of the present invention is an MMP-2 inhibitor with high affinity and yet with high specificity.

The present specification encompasses the contents disclosed in the specification and/or drawings of Japanese Patent Application No. 2008-262415 based on which the present application claims priority.

BEST MODE FOR CARRYING OUT THE INVENTION

Hereinbelow, embodiments of the present invention will be described in detail.

The present invention provides a fusion molecule comprising a β-amyloid precursor protein molecule-derived domain having an activity of selectively inhibiting matrix metalloproteinase-2 (APP-IP) and a tissue inhibitor of metalloproteinase (TIMP) capable of binding to latent matrix metalloproteinase-2 (latent MMP-2).

APP-IP is a partial amino acid sequence (ISYGNDALMP) in β-amyloid precursor protein molecule and has MMP-2 selective inhibitory activity (THE JOURNAL OF BIOLOGICAL CHEMISTRY, Vol. 278, No. 16, April 18, pp. 14020-14028, 2003). This APP-IP inhibits MMP-2 activity in a different inhibition mode than conventional hidroxamic add-based MMP inhibitors or natural inhibitor proteins TIMPs. Briefly, in the interaction with the substrate recognition site of MMP-2, hidroxamic acid-based MMP inhibitors and TIMPs interact in the N-terminus to C-terminus direction which is similar to the direction in the substrate peptide, whereas APP-IP interacts in the opposite N-terminus to C-terminus direction (THE JOURNAL OF BIOLOGICAL CHEMISTRY, Vol. 283, No. 15, April 11, pp. 10068-10078, 2008).

APP-IP is preferably derived from human. However, APP-IP may be derived from other mammals such as mouse, rat, hamster, rabbit, cat, dog, cattle, horse, sheep, monkey or the like.

Human MMP-2 is biosynthesized in cells and then secreted extracellularly. Immediately after the secretion, human MMP-2 consists of 631 amino acid residues and has an intramolecular inhibitor domain consisting of 80 amino acid residues called "propeptide domain" on its N-terminal side. This type of MMP-2 is designated "latent" MMP-2. Latent MMP-2 does not have enzyme activity because it has the propeptide domain. Also, it is impossible for inhibitors such as TIMPs to bind to the catalytic activity site of latent MMP-2. On the other hand, once the propeptide domain has been cut off and removed from latent MMP-2 as a result of the action of other proteinases, the intramolecular inhibitor is peeled off and the resultant MMP-2 acquires enzyme activity. The MMP-2 from which the N-terminal 80 amino acid residues of latent MMP-2 have been removed and which now consists of 551 amino acid residues is designated active MMP-2.

Examples of TIMP capable of binding to latent MMP-2 include tissue inhibitors of metalloproteinase-2, -3 and -4 (TIMP-2, -3 and -4). A C-terminal region of TIMP-2, -3 and -4 is capable of binding to the hemopexin-like domain of MMP-2.

Tissue inhibitor of metalloproteinase-2 (TIMP-2) is a physiological protein inhibitor against MMPs and has inhibitory activity against almost all MMPs (Murphy, G, and Nagase, H. (2006) Cardiovasc. Res. 69, 562-573). On the other hand, TIMP-2 promotes the activation of latent MMP-2 catalyzed by membrane type 1 MMP (MT1-MMP). The mode of action of this activation promotion by TIMP-2 is as follows. First, latent MMP-2 forms a trimolecular complex together with TIMP-2 and MT1-MMP and is concentrated on cell membranes during this process. In the trimolecular complex, the inhibitor activity site of TIMP-2 (N-terminal region) is bound to the active site of MT1-MMP; and the hemopexin-like domain of latent MMP-2 is bound to a C-terminal region of TIMP-2 (which is not an inhibitor activity site). Subsequently, the latent MMP-2 concentrated on cell membranes is activated by MT1-MMP molecules through limited proteolysis which are on the same cell membranes but to which TIMP-2 is not bound (Strongin, A. Y., Collier, I., Bannikov, G, Manner B. L., Grant, G. A., and Goldberg, G. I. (1995). *J. Biol. Chem.* 270, 5331-5338).

TIMP-2 nucleotide sequence (Registration No. NM003255.4; Database: NCBI) (SEQ ID NO: 3)

TIMP-2 amino acid sequence (Registration No. NP003246.1; Database: NCBI) (SEQ ID NO: 4)

The amino acid sequence and nucleotide sequence of human TIMP-2 are shown in SEQ ID NOS: 4 and 3, respectively. TIMP-2 is biosynthesized in cells and secreted extracellularly after cleavage of its signal peptide (to thereby yield a mature type TIMP-2 having activity). Immediately after the biosynthesis, Met is positioned at the N-terminus; after the secretion, however, the $27^{th}$ amino acid (Cys) comes to the first position. It is a usual practice to number the amino acid residues of TIMP-2 based on the mature type TIMP-2. The amino acid sequence of SEQ ID NO: 4 includes an N-terminal signal peptide (positions 1 to 26). SEQ ID NO: 3 is the nucleotide sequence of a DNA encoding the amino acid sequence of SEQ ID NO: 4.

Similar to TIMP-2, tissue inhibitors for metalloproteinase-3 and -4 (TIMP-3 and TIMP-4) are also physiological protein inhibitors against MMPs and have inhibitory activity against almost all MMPs. Further, TIMP-3 also inhibits the activities of metalloproteinases such as ADAM10, ADAM12, ADAM17 and ADAM-TS1, ADAM-TS4, ADAM-TS5 that belong to families other than MMPs. Further, similar to TIMP-2, both TIMP-3 and TIMP-4 are capable of binding to MMP-2 at a site other than its catalytic activity site (Murphy, G., and Nagase, H. (2006) Cardiovasc. Res. 69, 562-573).

TIMP-3 nucleotide sequence (Registration No. NM_000362.4; Database: NCBI) (SEQ ID NO: 10)

TIMP-3 amino acid sequence (Registration No. NP_000353.1; Database: NCBI) (SEQ ID NO: 11)

TIMP-4 nucleotide sequence (Registration No. NM_003256.2; Database: NCBI) (SEQ ID NO: 12)

TIMP-4 amino acid sequence (Registration No. NP_003247.1; Database: NCBI) (SEQ ID NO: 13)

The amino acid sequence and nucleotide sequence of human TIMP-3 are shown in SEQ ID NOS: 11 and 10, respectively. TIMP-3 is biosynthesized in cells and secreted extracellularly after cleavage of its signal peptide (to thereby yield a mature type TIMP-3 having activity). Immediately after the biosynthesis, Met is positioned the its N-terminus; after the secretion, however, the $24^{th}$ amino acid (Cys) comes to the first position. It is a usual practice to number the amino acid residues of TIMP-3 based on the mature type TIMP-3. The amino acid sequence of SEQ ID NO: 11 includes an N-terminal signal peptide (positions 1 to 23). SEQ ID NO: 10 is the nucleotide sequence of a DNA encoding the amino acid sequence of SEQ ID NO: 11.

The amino acid sequence and nucleotide sequence of human TIMP-4 are shown in SEQ ID NOS: 13 and 12, respectively. TIMP-4 is biosynthesized in cells and secreted extracellularly after cleavage of its signal peptide (to thereby yield a mature type TIMP-4 having activity). Immediately after the biosynthesis, Met is positioned at the N-terminus; after the secretion, however, the 30$^{th}$ amino acid (Cys) comes to the first position. It is a usual practice to number the amino acid residues of TIMP-4 based on the mature type TIMP-4. The amino acid sequence of SEQ ID NO: 13 includes an N-terminal signal peptide (positions 1 to 29). SEQ ID NO: 12 is the nucleotide sequence of a DNA encoding the amino acid sequence of SEQ ID NO: 11.

TIMP-2, -3 and -4 are preferably derived from human. However, they may be derived from other mammals such as mouse, rat, hamster, rabbit, cat, dog, cattle, horse, sheep, monkey or the like.

APP-IP may have 1 to 10, preferably 1 to 6, more preferably 1 to 3 amino acids added to its N-terminus and/or C-terminus. Such addition of amino acids is performed for the following purposes. Addition of amino acids to the N-terminus is performed to prevent the cleavage of the signal peptidase within APP-IP sequence during biosynthesis of the fusion protein of the invention in eukaryotic cells; and to prevent deletion of APP-IP portion that might occur in the body by the action of amino peptidase. On the other hand, insertion of glycine residues to the C-terminus is performed to introduce a highly flexible spacer between the body of TIMP capable of binding to latent MMP-2 and the APP-IP portion so that the APP-IP portion positioned on the N-terminal side of the TIMP capable of binding to latent MMP-2 can effectively be brought closer to the active site of MMP-2 as a C-terminal region of the TIMP capable of binding to latent MMP-2 binds to the hemopexin-like domain of MMP-2.

Preferable examples of amino acids or peptides to be added to the N-terminus of APP-IP include but are not limited to AGG, AGGG, AAGG and AAGGG. Preferable examples of amino acids or peptides to be added to the C-terminus of APP-IP include but are not limited to GG, GGG and GGGG.

The TIMP capable of binding to latent MMP-2 may be added to the C-terminus of APP-IP.

The present inventor has made it clear that the fusion protein composed of APP-IP and a TIMP capable of binding to latent MMP-2 works as an MMP-2 inhibitor of high affinity and high specificity because the MMP-2 binding site of the TIMP capable of binding to latent MMP-2 and the MMP-2 selective inhibition site of APP-IP are utilized in a complementary manner (see the Example described later). The catalytic activity of MMP-2 and the inhibitory effect upon that activity can be measured using a fluorescence quenching type synthetic peptide substrate in accordance with the methods described in prior art literature (THE JOURNAL OF BIOLOGICAL CHEMISTRY, Vol. 278, No. 16, April 18, pp. 14020-14028, 2003).

The amino acid sequence of one example of the fusion protein composed of APP-IP and a TIMP capable of binding to latent MMP-2 (fusion protein composed of APP-IP and TIMP-2 prepared in the Example described later) is shown in SEQ ID NO: 6. This amino acid sequence has the signal sequence of TIMP-2 at its N-terminus (positions 1 to 26). Further, APP-IP has the amino acid sequence AAGG added to its N-terminus and the amino acid sequence GGG added to its C-terminus. After the fusion protein consisting of the amino acid sequence of SEQ ID NO: 6 is biosynthesized in cells, it is secreted extracellularly upon cleavage of the signal sequence (positions 1 to 26) (to thereby yield a mature type protein). The amino acid sequence of the mature type protein is shown in SEQ ID NO: 7. The "fusion molecule composed of APP-IP and a TIMP capable of binding to latent MMP-2" according to the present invention encompasses not only the mature type protein but also those proteins which comprise the signal sequence.

Variants retaining the function of the fusion protein composed of APP-IP and a TIMP capable of binding to latent MMP-2 are also included in the present invention. Examples of such variants include those proteins which comprise the amino acid sequence of the fusion protein composed of APP-IP and a TIMP capable of binding to latent MMP-2, provided that they have a deletion, substitution or addition of one or several (usually 50 or less, preferably 10 or less) amino acids and which yet have a similar biological activity to the fusion protein composed of APP-IP and a TIMP capable of binding to latent MMP-2. The biological activity of the fusion protein composed of APP-IP and a TIMP capable of binding to latent MMP-2 may be exemplified by MMP-2 inhibitor activity.

The fusion protein composed of APP-IP and a TIMP capable of binding to latent MMP-2 may be prepared by known methods. For example, a DNA encoding the fusion protein composed of APP-IP and a TIMP capable of binding to latent MMP-2 is obtained; the resultant DNA is incorporated into an appropriate expression vector, which is then introduced into an appropriate host. The thus transformed host is cultured to produce the fusion protein as a recombinant protein. Thus, the fusion protein can be prepared. (See, for example, Current Protocols compact version: Molecular Biology Experimental Protocols I, II and III, jointly translated by Kaoru Saigo and Yumiko Sano, published by Maruzen; original book: Ausubel, F. M. et al., Short Protocols in Molecular Biology, Third Edition, John Wiley & Sons, Inc., New York).

Alternatively, the fusion protein of the present invention may be prepared in accordance with known methods of peptide synthesis.

Further, the present invention provides a DNA encoding the fusion protein composed of APP-IP and a TIMP capable of binding to latent MMP-2.

An isolated DNA encoding the fusion protein composed of APP-IP and a TIMP capable of binding to latent MMP-2 may be any DNA as long as it comprises a nucleotide sequence encoding the fusion protein composed of APP-IP and a TIMP capable of binding to latent MMP-2. Specific examples of this DNA include, but are not limited to, a DNA represented by the nucleotide sequence of SEQ ID NO: 5 and a DNA which hybridizes under stringent conditions to a DNA complementary to a DNA (e.g., DNA represented by the nucleotide sequence of SEQ ID NO: 5) encoding a fusion protein consisting of the amino acid sequence of SEQ ID NO: 6 (amino acid sequence of a fusion protein composed of human-derived APP-IP and TIMP-2) and which encodes a protein that has a similar biological activity to the fusion protein composed of APP-IP and a TIMP capable of binding to latent MMP-2 (e.g., TIMP-2). The biological activity of the fusion protein composed of APP-IP and a TIMP capable of binding to latent MMP-2 (e.g., TIMP-2) may be exemplified by MMP-2 inhibitor activity.

The DNA which hybridizes under stringent conditions to a DNA complementary to a DNA encoding a fusion protein consisting of the amino acid sequence of SEQ ID NO: 6 may have at least 80% (preferably at least 95%, more preferably at least 98%) identity with the whole or a part of the DNA complementary to the DNA encoding the fusion protein consisting of the amino acid sequence of SEQ ID NO: 6. Hybridization is performed under stringent conditions. The stability of a double stranded or hybrid nucleic acid is represented by melting temperature (Tm; the temperature at which a probe is dissociated from a target DNA). This melting temperature is used to define stringent conditions. If it is assumed that 1% mismatch decreases Tm by 1° C., the temperature of the final washing in hybridization reaction must be lowered. For example, when a nucleotide sequence having 95% or more identity with the probe is to be obtained, the temperature of the final washing must be lowered by 5° C. Actually, Tm will vary in the range from 0.5 to 1.5° C. for 1% mismatch. Examples of stringent conditions include hybridization in 5×SSC/5×Denhardt's solution/1.0% SDS at 68° C. and washing in 0.2×SSC/0.1% SDS at room temperature. Examples of moderately stringent conditions include washing in 3×SSC at 42° C. Salt concentrations and temperatures may be altered in order to achieve an optimum level of identity between the probe and the target nucleic acid. For further guides on such conditions, see Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons. N.Y.) at Unit 2.10.

The DNA encoding a fusion protein consisting of the amino acid sequence of SEQ ID NO: 6 may be exemplified by a DNA represented by the nucleotide sequence of SEQ ID NO: 5.

An isolated DNA encoding the fusion protein composed of APP-IP and a TIMP capable of binding to latent MMP-2 (e.g., TIMP-2) according to the present invention may, for example, be prepared as described below. Briefly, a DNA encoding human TIMP-2 is digested at restriction enzyme sites Eco52 I and Pst I contained in its nucleotide sequence (SEQ ID NO: 3). Subsequently, a pair of complementary synthetic DNA strands [sense strand:
5'-GGCCGACGCCGCCGCAGGAGGAATTAGT-TATGGTAATGATGCATTAATGCCAG GAGGAGGCT-GCA-3' (SEQ ID NO: 8) and anti-sense strand:
5'-GCCTCCTCCTGGCATTAATGCATCAT-TACCATAACTAATTCCTCCTGCGGCGGC GTC-3' (SEQ ID NO: 9)] as annealed into a double helix are inserted between the two restriction sites with a DNA ligase. The resultant DNA is introduced into *E. coli* for cloning.
Thus, the DNA of interest can be prepared.

A DNA encoding a variant of the fusion protein composed of APP-IP and a TIMP capable of binding to latent MMP-2 (e.g., TIMP-2) may be prepared by mutagenizing a desired site in the coding region of the fusion protein by targeted point mutagenesis. The mutagenized coding region of the fusion protein is amplified by PCR. The resultant PCR product is a DNA encoding a variant of the fusion protein composed of APP-IP and a TIMP capable of binding to latent MMP-2 (e.g., TIMP-2).

The present invention provides a vector comprising a DNA encoding the fusion protein composed of APP-IP and a TIMP capable of binding to latent MMP-2.

A recombinant vector comprising a DNA encoding the fusion protein composed of APP-IP and a TIMP capable of binding to latent MMP-2 may be obtained by inserting the DNA into an appropriate expression vector by known methods (e.g., methods described in Molecular Cloning 2nd Edition, J. Sambrook et al., Cold Spring Harbor Lab. Press, 1989).

Expression vectors that may be used include *Escherichia coli*-derived plasmids (e.g., pBR322, pBR325, pUC12, pUC13 or pGACAG); *Bacillus subtilis*-derived plasmids (e.g., pUB110, pTP5 or pC194), yeast-derived plasmids (e.g., pSH19 or pSH15); bacteriophages such as λ phage; animal viruses such as retrovirus, adenovirus or vaccinia virus; or insect pathogen viruses such as baculovirus.

The expression vector may also comprise promoters, enhancers, splicing signals, poly-A addition signals, selection markers, SV40 replication origins, and so forth.

The expression vector may be a fusion protein expression vector. Various fusion protein expression vectors are commercially available. For example, pGEX series (Amersham Pharmacia Biotech), pET CBD Fusion System 34b-38b (Novagen), pET Dsb Fusion Systems 39b and 40b (Novagen) and pET GST Fusion System 41 and 42 (Novagen) may be enumerated.

A transformant may be obtained by introducing into a host a recombinant vector comprising a DNA encoding the fusion protein composed of APP-IP and a TIMP capable of binding to latent MMP-2. The present invention also provides a transformant comprising a recombinant vector comprising a DNA encoding the fusion protein composed of APP-IP and a TIMP capable of binding to latent MMP-2.

Examples of the host include, but are not limited to, bacterial cells (such as *Escherilia* bacteria, *Bacillus* bacteria or *Bacillus subtilis*), fungal cells (such as yeast or *Aspergillus*), insect cells (such as S2 cells or Sf cells), animal cells (such as CHO cells, COS cells, HeLa cells, C127 cells, 3T3 cells, MK cells or HEK 293 cells), and plant cells.

Introduction of a recombinant vector into a host may be performed by the methods described in Molecular Cloning 2nd Edition, J. Sambrook et al., Cold Spring Harbor Lab. Press, 1989 (e.g., the calcium phosphate method, the DEAE-dextran method, transfection, microinjection, lipofection, electroporation, transduction, scrape loading, the shotgun method, etc.) or by infection.

The transformant may be cultured in a medium and the fusion protein composed of APP-IP and a TIMP capable of binding to latent MMP-2 may be collected from the resultant culture. When the fusion protein is secreted into the medium, the medium may be recovered, followed by isolation and purification of the fusion protein from the medium. When the fusion protein is produced within transformed cells, the cells may be lysed, followed by isolation and purification of the fusion protein from the cell lysate.

When the fusion protein is expressed in the form of a fusion protein with a tag, the tagged fusion protein may be isolated/purified and then treated with Factor Xa or an enzyme (enterokinase) to thereby cut off the tag. Thus, the fusion protein of interest may be obtained.

Isolation and purification of the fusion protein may be performed by known methods. Known isolation/purification methods which may be used in the present invention include, but are not limited to, methods using difference in solubility (such as salting-out or solvent precipitation); methods using difference in molecular weight (such as dialysis, ultrafiltration, gel filtration or SDS-polyacrylamide gel electrophoresis); methods using difference in electric charge (such as ion exchange chromatography); methods using specific affinity (such as affinity chromatography); methods using difference in hydrophobicity (such as reversed phase high performance liquid chromatography); and methods using difference in isoelectric point (such as isoelectric focusing).

The fusion protein composed of APP-IP and a TIMP capable of binding to latent MMP-2 may be used as a medicine such as cancer metastasis and/or angiogenesis inhibitor, or therapeutic and/or prophylactic for cardiovascular diseases (e.g., myocardial infarction, arteriosclerosis and hypertrophic cardiomyopathy). Further, the fusion protein composed of APP-IP and a TIMP capable of binding to latent MMP-2 may be applicable as a matrix metalloproteinase-2 inhibitor in vivo or in vitro for medical or reagent use. The present invention also provides a pharmaceutical composition, a cancer metastasis and/or angiogenesis inhibitor, a therapeutic and/or prophylactic for cardiovascular diseases, and a matrix metalloproteinase-2 inhibitor, each of which comprises the fusion protein composed of APP-IP and a TIMP capable of binding to latent MMP-2.

Since the fusion protein composed of APP-IP and a TIMP capable of binding to latent MMP-2 is an inhibitor specific to matrix metalloproteinase-2 (MMP-2), it is applicable as a reagent for basic studies of MMP-2 such as analysis of its physiological functions.

It has been suggested that MMP-2 is potentially involved in diseases of the cardiovascular system (e.g., acute myocardial infarction) as well as in cancer invasion/metastasis and angiogenesis in tumor tissue. Therefore, the fusion protein composed of APP-IP and a TIMP capable of binding to latent MMP-2 is applicable as a therapeutic for these diseases in which MMP-2 is involved.

When the fusion protein composed of APP-IP and a TIMP capable of binding to latent MMP-2 is used as a cancer metastasis and/or angiogenesis inhibitor, or a therapeutic and/or prophylactic for cardiovascular diseases (e.g., myocardial infarction, arteriosclerosis and hypertrophic cardiomyopathy), it may be administered either alone or together with pharmacologically acceptable carriers, diluents or excipients as pharmaceutical compositions of appropriate dosage form to mammals (e.g. human, rabbit, dog, cat, rat, mouse, etc.) orally or parenterally. Dose levels may vary depending on the patient to be treated, the target disease, symptoms, administration route, and so on. For example, when the fusion protein is used as a cancer metastasis and/or angiogenesis inhibitor, it may be injected subcutaneously (preferably, consecutively or every other day) at a dose of 0.001-10 mg/kg body weight, preferably 0.01-1 mg/kg body weight, per administration about seven times a week, preferably at a frequency of about once a day. In other use or in other parenteral administration (e.g., nasal administration) and oral administration, similar dose levels may be used. If symptoms are particularly severe, the dose may be increased accordingly.

Compositions for oral administration include solid or liquid preparations such as tablets (including sugar-coated tablets and film-coated tablets), pills, granules, dispersants, capsules (including soft capsules), syrups, emulsions, and suspensions. These compositions may be prepared by conventional methods and may contain carriers, diluents or excipients conventionally used in the field of medicine manufacture. For example, lactose, starch, sucrose, magnesium stearate and the like may be used as carriers or excipients for tablets.

Compositions for parenteral administration include, for example, injections and suppositories. Injections include intravenous injections, subcutaneous injections, intradermal injections, muscle injections, instilment injections, etc. Such injections may be prepared by conventional methods, i.e., by dissolving, suspending or emulsifying the fusion protein of the present invention in an aseptic, aqueous or oily liquid conventionally used in injections. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80™, HCO-50 (polyoxyethylene (50 mol)

adduct of hydrogenated castor oil)], etc. Examples of oily liquids for injection include sesame oil and soybean oil. They may be used in combination with an auxiliary solubilizer such as benzyl benzoate, benzyl alcohol, etc. Usually, the prepared injections are filled in appropriate ampoules. Suppositories for administration into the rectum may be prepared by mixing the fusion protein composed of APP-IP and a TIMP capable of binding to latent MMP-2 with a conventional suppository base.

It is convenient to formulate the above-described pharmaceutical compositions for oral or parenteral administration into unit dosage forms that would give an appropriate dose of the active ingredient. Examples of such unit dosage forms include tablet, pills, capsules, injections (ampoules), and suppositories. It is usually preferred that 0.01 to 1 mg of the fusion protein composed of APP-IP and a TIMP capable of binding to latent MMP-2 be contained in each unit dosage form. The content of the active ingredient in a prepared unit dosage form varies depending on the type of the preparation. The content of the active ingredient is usually 1 to 100% by weight, preferably 50 to 100% by weight.

The above-described pharmaceutical compositions may contain other active ingredients as long as they do not cause any undesirable interaction when they are combined with the fusion protein composed of APP-IP and a TIMP capable of binding to latent MMP-2.

EXAMPLES

Hereinbelow, the present invention will be described in detail with reference to the following Example. However, the present invention is not limited to this Example.

Example 1

Method of Preparation of APP-IP-TIMP-2 Fusion Protein: A DNA encoding APP-IP-TIMP-2 fusion protein was prepared by digesting a DNA encoding human TIMP-2 at restriction enzyme sites Eco52 I and Pst I contained in its nucleotide sequence (SEQ ID NO: 3) and inserting a pair of complementary synthetic DNA strands [sense strand: 5'-GGCCGACGCCGCCGCAGGAGGAATTAGT-TATGGTAATGATGCATTAATGCCAG GAGGAGGCT-GCA-3' (SEQ ID NO: 8) and anti-sense strand: 5'-GCCTCCTCCTGGCATTAATGCATCAT-TACCATAACTAATTCCTCCTGCGGCGGC GTC-3' (SEQ ID NO: 9)] as annealed into a double helix between the two restriction enzyme sites with a DNA ligase. This DNA encoding the fusion protein was inserted into an animal cell expression vector pcDNA3.1/Zeo(−) (Invitrogen) or an E. coli expression vector pFLAG-CTC (Sigma) at their multi-cloning site. APP-IP-TIMP-2 fusion protein was expressed in cells as an inclusion body by culturing E. coli DH5α transformed with the above-described vector (APP-IP-TIMP-2-pFLAG-CTC) in the presence of 1 mM isopropyl-β-D-thiogalactopylanoside at 37° C. for 5 hours. The resultant cells were disrupted by sonication and centrifuged to thereby recover the inclusion body. The APP-IP-TIMP-2 fusion protein thus recovered as the inclusion body was dissolved in 50 mM Tris-HCl (pH 8.0) containing 6M guanidinium hydrochloride, 20 mM dithiothreitol and 5 mM EDTA and centrifuged to remove impurities. Subsequently, the fusion protein was rapidly diffused in 100 volumes of a refolding buffer (50 mM Tris-HCl (pH 8.0), 1 M arginine, 5 mM reduced glutathione, 1 mM oxidized glutathione and 5 mM EDTA) and incubated at 4° C. for 48 hours. Thus, its conformation and intramolecular disulfide bonds were formed. From the resultant sample, arginine was removed by dialysis. Then, APP-IP-TIMP-2 fusion protein in which intramolecular disulfide bonds had been formed was isolated and purified by reversed phase HPLC.

Method of Measurement of Inhibitory Activities upon MMP-2, MMP-9, MMP-7 and MT1-MMP Catalytic Domains: The catalytic activities of MMP-2, MMP-7, MMP-9 and MT1-MMP catalytic domains and inhibitory effects upon their activities were measured using a fluorescence quenching type synthetic peptide substrate in accordance with prior art literature (THE JOURNAL OF BIOLOGICAL CHEMISTRY, Vol. 278, No. 16, April 18, pp. 14020-14028, 2003).

Results and Discussion

Figure 1:
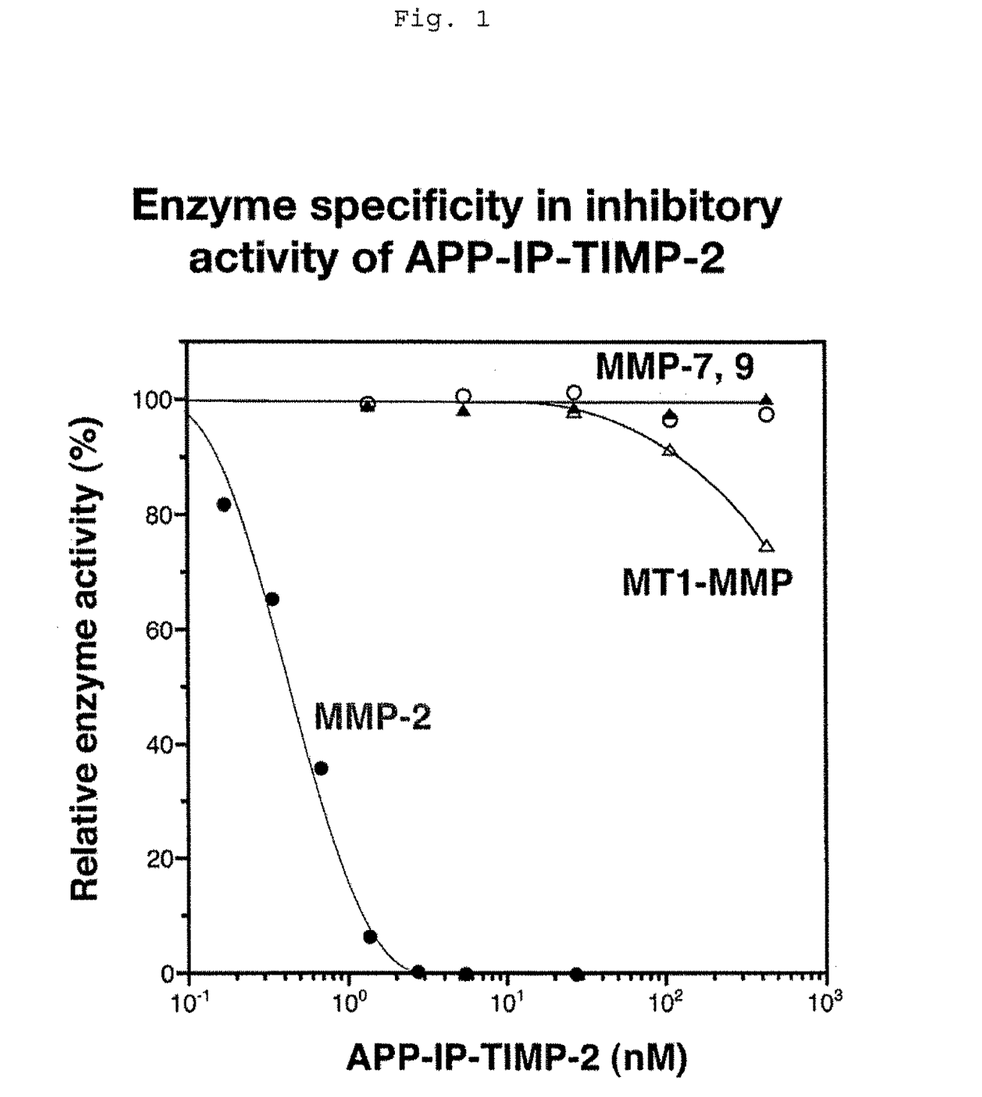
FIG. 1 is a graph showing the inhibitory activities of APP-IP-TIMP-2 fusion protein against MMP-2 and MMP-9.

The results of examination of the inhibitory effects of APP-IP-TIMP-2 fusion protein upon the synthetic peptide substrate hydrolysis activities of MMP-2, MMP-7, MMP-9 and MT1-MMP catalytic domains revealed that the activity of MMP-2 was strongly inhibited by this fusion protein and that the $IC_{50}$ (inhibitor concentration that reduces a specified activity to 50% of its former level) was about 0.4 nM. Further, the activity of MMP-2 was almost completely inhibited in the presence of 2 nM APP-IP-TIMP-2. In contrast, it was revealed that the activities of MMP-7 and MMP-9 were kept almost 100% in the presence of 400 nM APP-IP-TIMP-2; i.e., they were not inhibited at all (FIG. 1). Further, it was revealed that about 75% of the activity of MT1-MMP catalytic domain was retained in the presence of 400 nM APP-IP-TIMP-2, showing that the inhibitory effect of APP-IP-TIMP-2 upon MT1-MMP was less than 1/1000 of its inhibitory effect upon MMP-2. On the other hand, prior art literature (THE JOURNAL OF BIOLOGICAL CHEMISTRY, Vol. 278, No. 16, April 18, pp. 14020-14028, 2003) disclosed the inhibitory activities of APP-IP upon the synthetic peptide substrate hydrolysis activities of MMP-2, MMP-7, MMP-9 and MT1-MMP catalytic domains; the reported $IC_{50}$ values of APP-IP were 30 nM, 15 µM, 20 µM and 2 µM, respectively. Therefore, it was found that APP-IP-TIMP-2 has about 75 times higher MMP-2 inhibitory activity than APP-IP, whereas APP-IP-TIMP-2 and APP-IP have almost equal inhibitory effect upon other MMPs. These results suggest that being assisted by the binding of a C-terminal region of TIMP-2 portion to the hemopexin-like domain of MMP-2, interaction between the APP-IP portion and the catalytic activity site of MMP-2 was significantly enhanced in the interaction between APP-IP-TIMP-2 fusion protein and MMP-2. Further, it has been reported that TIMP-2 has a high inhibitory activity against both MMP-2 and MMP-9, with the respective inhibition constants being 7.2 nM and 43 nM. (Olson, M. W., Gervasi, D. C., Mobashery, S., and Fridman, R. (1997) *J. Biol. Chem.* 272, 29975-29983). From this, it is believed that the fact that APP-IP-TIMP-2 did not inhibit MMP-9 at the concentration of 400 nM suggests that the inhibitory activity against MMPs which TIMP-2 naturally possesses has been completely eliminated by the addition of APP-IP to the N-terminus of TIMP-2. These results are well consistent with the following reports made previously: coordination of the α-amino group of the N-terminal Cys 1 of TIMP-2 to the zinc ion at the activity center of MMP is important for the inhibitory activity of TIMP-2 (Fernandez-Catalan, C., Bode, W., Huber, R., Turk, D., Calvete, J. J., Lichte, A., Tschesche, H., and Maskos, K. (1998) *EMBO J.* 17, 5238-5248); when this α-amino group is chemically modified (Higashi, S., and Miyazaki, K. (1999) *J. Biol. Chem.* 274, 10497-10504), or when one alanine residue is added to the N-terminus of TIMP-2 (Wingfield, P. T., Sax, 3. K., Stahl, S. J., Kaufman, J., Palmer, I., Chung, V., Corcoran, M. L., Kleiner, D. E., and Stetler-Stevenson, W. G. (1999) *J. Biol. Chem.* 274,21362-21368), the MMPs inhibitor activity of TIMP-2 is eliminated. The above-described results revealed that when APP-IP is added to the N-terminus of TIMP-2, TIMP-2's MMP inhibitory activity with low specificity is lost and, at the same time, interaction between APP-IP and the catalytic site of MMP-2 is enhanced, yielding an inhibitor with high affinity and specificity for MMP-2.

MMPs are good target molecules for developing cancer metastasis inhibitors and cancer growth inhibitors. To date, a large number of MMP inhibitors based on hydroxamic acid derivatives have been developed by pharmaceutical companies, etc. However, it has been found that because of their low specificity, these conventionally developed MMP inhibitors inhibit not only their target MMP but also other MMPs in the body, thus producing unexpected side effect. Besides, some of MMPs inhibit cancer invasion and metastasis. Therefore, if inhibitors with low specificity inhibit all MMPs, the effect of inhibition of their target MMP will be offset and, even worse, there is a possibility that cancer metastasis might be enhanced (Overall, C. M., and Kleifeld, O. (2006) *Nat. Rev. Cancer* 6, 227-239). Given these facts, there is high likelihood that APP-IP-TIMP-2 with high specificity for MMP-2 can be a cancer metastasis inhibitor or cancer growth inhibitor with an extremely small adverse effect. Further, the results of analyses using knockout mice revealed no apparent disorders in MMP-2 deficient mice (Itoh, T., Ikeda, T., Gomi, H., Nakao, S., Suzuki, T., and Itohara, S. (1997) *Biol. Chem.* 272, 22389-22392). On the other hand, it was reported that angiogenesis in tumor tissue was significantly inhibited in MMP-2 deficient mice (Ito, T. et al. (1998) *Cancer Res.* 58, 1048-1051). From these reports, too, it can be highly expected that APP-IP-TIMP-2 will produce less adverse effects in treatment targeting MMP-2 while producing great effects in inhibiting angiogenesis in cancer tissue with subsequent inhibition of cancer growth. Further, since cardiac rupture that would otherwise occur after acute myocardial infarction was inhibited in MMP-2 deficient mice (Matsumura, S., Iwanaga, S., Mochizuki, S., Okamoto, H., Ogawa, S., and Okada, Y. (2005) *J Clin Invest.* 115, 599-609) and development of cardiac hypertrophy induced by the load of blood pressure was inhibited in such mice (Matsusaka, H., Ide, T., Matsushima, S., Ikeuchi, M., Kubota, T., Sunagawa, K., Kinugawa, S., and Tsutsui, H. (2006) *Hypertension.* 47, 711-717), it is believed that APP-IP-TIMP-2 fusion protein is also applicable as a therapeutic and/or prophylactic for cardiovascular diseases.

All publications, patents and patent applications cited herein are incorporated herein by reference in their entirety.

Industrial Applicability

The fusion protein of the present invention is applicable as an MMP-2 inhibitor with high affinity and high specificity. It has been suggested that MMP-2 is potentially involved in diseases of the cardiovascular system (such as acute myocardial infarction) as well as in cancer invasion/metastasis and angiogenesis in tumor tissue. Therefore, the fusion protein of the present invention is also applicable as a therapeutic for these diseases in which MMP-2 is involved. Further, since specific inhibitors for individual MMPs have not been developed yet, the fusion protein of the present invention is also applicable as a reagent for basic studies of MMP-2 such as analysis of its physiological functions.

Sequence Listing Free Text

<SEQ ID NO: 1>

SEQ ID NO: 1 shows the nucleotide sequence of a DNA encoding human APP-IP (a region of $APP_{770}$ containing its residues 586 to 595).

<SEQ ID NO: 2>

SEQ ID NO: 2 shows the amino acid sequence of human APP-IP (a region of $APP_{770}$ containing its residues 586 to 595).

<SEQ ID NO: 3>

SEQ ID NO: 3 shows the nucleotide sequence of a DNA encoding human TIMP-2. This sequence is the nucleotide sequence of a DNA encoding the amino acid sequence of SEQ ID NO: 4 (amino acid sequence of human TIMP-2 which has a signal peptide (positions 1 to 26) at its N-terminus).

<SEQ ID NO: 4>

SEQ ID NO: 4 shows the amino acid sequence of human TIMP-2. This sequence has a signal peptide (positions 1 to 26) at its N-terminus.

<SEQ ID NO: 5>

SEQ ID NO: 5 shows the nucleotide sequence of a DNA encoding a fusion protein composed of human AAP-IP (a region of $APP_{770}$ containing its residues 586 to 595) and human TIMP-2 (the fusion protein prepared in the Example; The protein has a signal peptide at its N-terminus (positions 1 to 26), and APP-IP has the amino acid sequence AAGG added to its N-terminus and GGG added to its C-terminus).

<SEQ ID NO: 6>

SEQ ID NO: 6 shows the amino acid sequence of a fusion protein composed of human AAP-IP (a region of $APP_{770}$ containing its residues 586 to 595) and human TIMP-2 (the fusion protein prepared in the Example. The protein has a signal peptide at its N-terminus (positions 1 to 26), and APP-IP has the amino acid sequence AAGG added to its N-terminus and GGG added to its C-terminus).

<SEQ ID NO: 7>

SEQ ID NO: 7 shows the amino acid sequence of a fusion protein composed of a mature type (with the signal peptide cut off) human AAP-IP (a region of $APP_{770}$ containing its residues 586 to 595) and human TIMP-2.

<SEQ ID NO: 8>

SEQ ID NO: 8 shows the nucleotide sequence of the synthetic DNA strand (sense strand) used in the Example.

<SEQ ID NO: 9>

SEQ ID NO: 9 shows the nucleotide sequence of the synthetic DNA strand (anti-sense strand) used in the Example.

<SEQ ID NO: 10>

SEQ ID NO: 10 shows the nucleotide sequence of a DNA encoding human TIMP-3. This sequence is the nucleotide sequence of a DNA encoding the amino acid sequence of SEQ ID NO: 11 (the amino acid sequence of human TIMP-3 which has a signal peptide (positions 1 to 23) at its N-terminus).

<SEQ ID NO: 11>

SEQ ID NO: 11 shows the amino acid sequence of human TIMP-3. This sequence has a signal peptide (positions 1 to 23) at its N-terminus.

<SEQ ID NO: 12>

SEQ ID NO: 12 shows the nucleotide sequence of a DNA encoding human TIMP-4. This sequence is the nucleotide sequence of a DNA encoding the amino acid sequence of SEQ ID NO: 13 (the amino acid sequence of human TIMP-4 which has a signal peptide (positions 1 to 29) at its N-terminus).

<SEQ ID NO: 13>

SEQ ID NO: 13 shows the amino acid sequence of human TIMP-4. This sequence has a signal peptide (positions 1 to 29) at its N-terminus.

The invention claimed is:

1. A fusion molecule comprising a β-amyloid precursor protein molecule-derived domain and a tissue inhibitor of metalloproteinase capable of binding to latent matrix metalloproteinase-2, said fusion protein comprising the sequence of SEQ ID NO: 6 or 7.

2. A pharmaceutical composition comprising the fusion molecule according to claim 1.

* * * * *

```
                              SEQUENCE LISTING

<160> NUMBER OF SEQ ID NOS: 13

<210> SEQ ID NO 1
    <211> LENGTH: 30
    <212> TYPE: DNA
    <213> ORGANISM: Homo sapiens

<400> SEQUENCE: 1
attagttatg gtaatgatgc attaatgcca                                        30

<210> SEQ ID NO 2
    <211> LENGTH: 10
    <212> TYPE: PRT
    <213> ORGANISM: Homo sapiens

<400> SEQUENCE: 2

Ile Ser Tyr Gly Asn Asp Ala Leu Met Pro
    1               5                   10

<210> SEQ ID NO 3
    <211> LENGTH: 663
    <212> TYPE: DNA
    <213> ORGANISM: Homo sapiens

<400> SEQUENCE: 3
atgggcgccg cggcccgcac cctgcggctg gcgctcggcc tcctgctgct ggcgacgctg      60
cttcgcccgg ccgacgcctg cagctgctcc ccggtgcacc cgcaacaggc gttttgcaat     120
gcagatgtag tgatcagggc caaagcggtc agtgagaagg aagtggactc tggaaacgac     180
atttatggca accctatcaa gaggatccag tatgagatca gcagataaa gatgttcaaa      240 gggcctgaga aggatataga gtttatctac acggcccct cctcggcagt gtgtgggtc       300
```

```
tcgctggacg ttggaggaaa gaaggaatat ctcattgcag gaaaggccga gggggacggc    360
aagatgcaca tcaccctctg tgacttcatc gtgccctggg acaccctgag caccacccag    420
aagaagagcc tgaaccacag gtaccagatg ggctgcgagt gcaagatcac gcgctgcccc    480
atgatcccgt gctacatctc ctccccggac gagtgcctct ggatggactg ggtcacagag    540
aagaacatca acgggcacca ggccaagttc ttcgcctgca tcaagagaag tgacggctcc    600
tgtgcgtggt accgcggcgc ggcgcccccc aagcaggagt ttctcgacat cgaggaccca    660
taa                                                                 663
```

<210> SEQ ID NO 4
<211> LENGTH: 220
<212> TYPE: PRT
<213> ORGANISM: Homo sapiens

<400> SEQUENCE: 4

```
Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
                20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
        50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
    130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
    210                 215                 220
```

<210> SEQ ID NO 5
<211> LENGTH: 714
<212> TYPE: DNA
<213> ORGANISM: Artificial
<220> FEATURE:
<223> OTHER INFORMATION: DNA encoding fusion protein

<400> SEQUENCE: 5

```
atgggcgccg cggcccgcac cctgcggctg gcgctcggcc tcctgctgct ggcgacgctg     60
cttcgcccgg ccgacgccgc cgcaggagga attagttatg gtaatgatgc attaatgcca    120
ggaggaggct gcagctgctc cccggtgcac ccgcaacagg cgttttgcaa tgcagatgta    180
```

```
gtgatcaggg ccaaagcggt cagtgagaag gaagtggact ctggaaacga catttatggc    240
aaccctatca agaggatcca gtatgagatc aagcagataa agatgttcaa agggcctgag    300
aaggatatag agtttatcta cacggccccc tcctcggcag tgtgtggggt ctcgctggac    360
gttggaggaa agaaggaata tctcattgca ggaaaggccg aggggacgg caagatgcac    420 atcaccctct gtgacttcat cgtgccctgg acaccctga gcaccaccca gaagaagagc    480
ctgaaccaca ggtaccagat gggctgcgag tgcaagatca cgcgctgccc catgatcccg    540
tgctacatct cctccccgga cgagtgcctc tggatggact gggtcacaga gaagaacatc    600
aacgggcacc aggccaagtt cttcgcctgc atcaagagaa gtgacggctc ctgtgcgtgg    660
taccgcggcg cggcgccccc caagcaggag tttctcgaca tcgaggaccc ataa         714
```

<210> SEQ ID NO 6
<211> LENGTH: 237
<212> TYPE: PRT
<213> ORGANISM: Artificial
<220> FEATURE:
<223> OTHER INFORMATION: Fusion protein

<400> SEQUENCE: 6

```
Met Gly Ala Ala Ala Arg Thr Leu Arg Leu Ala Leu Gly Leu Leu Leu
1               5                   10                  15

Leu Ala Thr Leu Leu Arg Pro Ala Asp Ala Ala Ala Gly Gly Ile Ser
                20                  25                  30

Tyr Gly Asn Asp Ala Leu Met Pro Gly Gly Gly Cys Ser Cys Ser Pro
            35                  40                  45

Val His Pro Gln Gln Ala Phe Cys Asn Ala Asp Val Val Ile Arg Ala
        50                  55                  60

Lys Ala Val Ser Glu Lys Glu Val Asp Ser Gly Asn Asp Ile Tyr Gly
65                  70                  75                  80

Asn Pro Ile Lys Arg Ile Gln Tyr Glu Ile Lys Gln Ile Lys Met Phe
                85                  90                  95

Lys Gly Pro Glu Lys Asp Ile Glu Phe Ile Tyr Thr Ala Pro Ser Ser
            100                 105                 110

Ala Val Cys Gly Val Ser Leu Asp Val Gly Gly Lys Lys Glu Tyr Leu
        115                 120                 125

Ile Ala Gly Lys Ala Glu Gly Asp Gly Lys Met His Ile Thr Leu Cys
    130                 135                 140

Asp Phe Ile Val Pro Trp Asp Thr Leu Ser Thr Thr Gln Lys Lys Ser
145                 150                 155                 160

Leu Asn His Arg Tyr Gln Met Gly Cys Glu Cys Lys Ile Thr Arg Cys
                165                 170                 175

Pro Met Ile Pro Cys Tyr Ile Ser Ser Pro Asp Glu Cys Leu Trp Met
            180                 185                 190

Asp Trp Val Thr Glu Lys Asn Ile Asn Gly His Gln Ala Lys Phe Phe
        195                 200                 205

Ala Cys Ile Lys Arg Ser Asp Gly Ser Cys Ala Trp Tyr Arg Gly Ala
    210                 215                 220

Ala Pro Pro Lys Gln Glu Phe Leu Asp Ile Glu Asp Pro
225                 230                 235
```

<210> SEQ ID NO 7
<211> LENGTH: 211
<212> TYPE: PRT
<213> ORGANISM: Artificial

<220> FEATURE:
<223> OTHER INFORMATION: Mature form of fusion protein

<400> SEQUENCE: 7

Ala Ala Gly Gly Ile Ser Tyr Gly Asn Asp Ala Leu Met Pro Gly Gly
1               5                   10                  15
Gly Cys Ser Cys Ser Pro Val His Pro Gln Gln Ala Phe Cys Asn Ala
            20                  25                  30
Asp Val Val Ile Arg Ala Lys Ala Val Ser Glu Lys Glu Val Asp Ser
        35                  40                  45
Gly Asn Asp Ile Tyr Gly Asn Pro Ile Lys Arg Ile Gln Tyr Glu Ile
    50                  55                  60
Lys Gln Ile Lys Met Phe Lys Gly Pro Glu Lys Asp Ile Glu Phe Ile
65                  70                  75                  80
Tyr Thr Ala Pro Ser Ser Ala Val Cys Gly Val Ser Leu Asp Val Gly
                85                  90                  95
Gly Lys Lys Glu Tyr Leu Ile Ala Gly Lys Ala Glu Gly Asp Gly Lys
            100                 105                 110
Met His Ile Thr Leu Cys Asp Phe Ile Val Pro Trp Asp Thr Leu Ser
        115                 120                 125
Thr Thr Gln Lys Lys Ser Leu Asn His Arg Tyr Gln Met Gly Cys Glu
    130                 135                 140
Cys Lys Ile Thr Arg Cys Pro Met Ile Pro Cys Tyr Ile Ser Ser Pro
145                 150                 155                 160
Asp Glu Cys Leu Trp Met Asp Trp Val Thr Glu Lys Asn Ile Asn Gly
                165                 170                 175
His Gln Ala Lys Phe Phe Ala Cys Ile Lys Arg Ser Asp Gly Ser Cys
            180                 185                 190
Ala Trp Tyr Arg Gly Ala Ala Pro Pro Lys Gln Glu Phe Leu Asp Ile
        195                 200                 205
Glu Asp Pro
    210

<210> SEQ ID NO 8
<211> LENGTH: 65
<212> TYPE: DNA
<213> ORGANISM: Artificial
<220> FEATURE:
<223> OTHER INFORMATION: Synthetic DNA

<400> SEQUENCE: 8
ggccgacgcc gccgcaggag gaattagtta tggtaatgat gcattaatgc caggaggagg    60
ctgca                                                                65

<210> SEQ ID NO 9
<211> LENGTH: 57
<212> TYPE: DNA
<213> ORGANISM: Artificial
<220> FEATURE:
<223> OTHER INFORMATION: Synthetic DNA

<400> SEQUENCE: 9
gcctcctcct ggcattaatg catcattacc ataactaatt cctcctgcgg cggcgtc       57

<210> SEQ ID NO 10
<211> LENGTH: 636
<212> TYPE: DNA
<213> ORGANISM: Homo sapiens

<400> SEQUENCE: 10

```
atgacccctt ggctcgggct catcgtgctc ctgggcagct ggagcctggg ggactggggc    60
gccgaggcgt gcacatgctc gcccagccac ccccaggacg ccttctgcaa ctccgacatc   120
gtgatccggg ccaaggtggt ggggaagaag ctggtaaagg agggggccctt cggcacgctg   180
gtctacacca tcaagcagat gaagatgtac cgaggcttca ccaagatgcc ccatgtgcag   240
tacatccata cggaagcttc cgagagtctc tgtggcctta agctggaggt caacaagtac   300
cagtacctgc tgacaggtcg cgtctatgat ggcaagatgt acacggggct gtgcaacttc   360
gtggagaggt gggaccagct caccctctcc cagcgcaagg ggctgaacta tcggtatcac   420
ctgggttgta actgcaagat caagtcctgc tactacctgc cttgctttgt gacttccaag   480
aacgagtgtc tctggaccga catgctctcc aatttcggtt accctggcta ccagtccaaa   540
cactacgcct gcatccggca aagggcggc tactgcagct ggtaccgagg atgggccccc   600
ccggataaaa gcatcatcaa tgccacagac ccctga                             636
```

<210> SEQ ID NO 11
<211> LENGTH: 211
<212> TYPE: PRT
<213> ORGANISM: Homo sapiens

<400> SEQUENCE: 11

```
Met Thr Pro Trp Leu Gly Leu Ile Val Leu Leu Gly Ser Trp Ser Leu
1               5                   10                  15
Gly Asp Trp Gly Ala Glu Ala Cys Thr Cys Ser Pro Ser His Pro Gln
            20                  25                  30
Asp Ala Phe Cys Asn Ser Asp Ile Val Ile Arg Ala Lys Val Val Gly
        35                  40                  45
Lys Lys Leu Val Lys Glu Gly Pro Phe Gly Thr Leu Val Tyr Thr Ile
    50                  55                  60
Lys Gln Met Lys Met Tyr Arg Gly Phe Thr Lys Met Pro His Val Gln
65                  70                  75                  80
Tyr Ile His Thr Glu Ala Ser Glu Ser Leu Cys Gly Leu Lys Leu Glu
                85                  90                  95
Val Asn Lys Tyr Gln Tyr Leu Leu Thr Gly Arg Val Tyr Asp Gly Lys
            100                 105                 110
Met Tyr Thr Gly Leu Cys Asn Phe Val Glu Arg Trp Asp Gln Leu Thr
        115                 120                 125
Leu Ser Gln Arg Lys Gly Leu Asn Tyr Arg Tyr His Leu Gly Cys Asn
    130                 135                 140
Cys Lys Ile Lys Ser Cys Tyr Tyr Leu Pro Cys Phe Val Thr Ser Lys
145                 150                 155                 160
Asn Glu Cys Leu Trp Thr Asp Met Leu Ser Asn Phe Gly Tyr Pro Gly
                165                 170                 175
Tyr Gln Ser Lys His Tyr Ala Cys Ile Arg Gln Lys Gly Gly Tyr Cys
            180                 185                 190
Ser Trp Tyr Arg Gly Trp Ala Pro Pro Asp Lys Ser Ile Ile Asn Ala
        195                 200                 205
Thr Asp Pro
    210
```

<210> SEQ ID NO 12
<211> LENGTH: 675
<212> TYPE: DNA

<213> ORGANISM: Homo sapiens

<400> SEQUENCE: 12

```
atgcctggga gccctcggcc cgcgccaagc tgggtgctgt tgctgcggct gctggcgttg      60
ctgcggcccc cggggctggg tgaggcatgc agctgcgccc cggcgcaccc tcagcagcac     120
atctgccact cggcacttgt gattcgggcc aaaatctcca gtgagaaggt agttccggcc     180
agtgcagacc ctgctgacac tgaaaaaatg ctccggtatg aaatcaaaca gataaagatg     240
ttcaaagggt ttgagaaagt caaggatgtt cagtatatct atacgccttt tgactcttcc     300
ctctgtggtg tgaaactaga agccaacagc cagaagcagt atctcttgac tggtcaggtc     360
ctcagtgatg gaaaagtctt catccatctg tgcaactaca tcgagccctg ggaggacctg     420
tccttggtgc agagggaaag tctgaatcat cactaccatc tgaactgtgg ctgccaaatc     480
accacctgct acacagtacc ctgtaccatc tcggccccta acgagtgcct ctggacagac     540
tggctgttgg aacgaaagct ctatggttac caggctcagc attatgtctg tatgaagcat     600
gttgacggca cctgcagctg gtaccggggc acctgcctc tcaggaagga gtttgttgac     660
atcgttcagc cctag                                                     675
```

<210> SEQ ID NO 13
<211> LENGTH: 224
<212> TYPE: PRT
<213> ORGANISM: Homo sapiens

<400> SEQUENCE: 13

```
Met Pro Gly Ser Pro Arg Pro Ala Pro Ser Trp Val Leu Leu Arg
1               5                   10                  15

Leu Leu Ala Leu Leu Arg Pro Pro Gly Leu Gly Glu Ala Cys Ser Cys
            20                  25                  30

Ala Pro Ala His Pro Gln Gln His Ile Cys His Ser Ala Leu Val Ile
        35                  40                  45

Arg Ala Lys Ile Ser Ser Glu Lys Val Val Pro Ala Ser Ala Asp Pro
    50                  55                  60

Ala Asp Thr Glu Lys Met Leu Arg Tyr Glu Ile Lys Gln Ile Lys Met
65                  70                  75                  80

Phe Lys Gly Phe Glu Lys Val Lys Asp Val Gln Tyr Ile Tyr Thr Pro
                85                  90                  95

Phe Asp Ser Ser Leu Cys Gly Val Lys Leu Glu Ala Asn Ser Gln Lys
            100                 105                 110

Gln Tyr Leu Leu Thr Gly Gln Val Leu Ser Asp Gly Lys Val Phe Ile
        115                 120                 125

His Leu Cys Asn Tyr Ile Glu Pro Trp Glu Asp Leu Ser Leu Val Gln
    130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
            180                 185                 190

Gln His Tyr Val Cys Met Lys His Val Asp Gly Thr Cys Ser Trp Tyr
        195                 200                 205

Arg Gly His Leu Pro Leu Arg Lys Glu Phe Val Asp Ile Val Gln Pro
    210                 215                 220
```